United States Patent [19]
Stroppolo et al.

[11] Patent Number: 5,869,102
[45] Date of Patent: Feb. 9, 1999

[54] SOLID PHARMACEUTICAL COMPOSITIONS CONTAINING (S)-2-(4-ISOBUTYLPHENYL) PROPIONIC ACID ACTIVE INGREDIENT AND MICROCRYSTALLINE CELLULOSE AND COLLOIDAL SILICA AS EXCIPIENTS

[75] Inventors: Federico Stroppolo, Pregassona, Switzerland; Daniele Bonadeo, Varese, Italy; Alberto Pagano, Cinisello Balsamo, Italy; Annibale Gazzaniga, deceased, late of Rescaldina, Italy, by Cisella Adele Marabelli Gazzaniga, Giovanni Battista Gazzaniga, legal representatives; Paola Maria Gazzaniga, legal representative, Busto Artsizio, Italy

[73] Assignee: Zambon Group, S.p.A., Milan, Italy

[21] Appl. No.: 750,201

[22] PCT Filed: May 26, 1995

[86] PCT No.: PCT/EP95/02010

§ 371 Date: Nov. 27, 1996

§ 102(e) Date: Nov. 27, 1996

[87] PCT Pub. No.: WO95/35104

PCT Pub. Date: Dec. 28, 1995

[30] Foreign Application Priority Data

Jun. 17, 1994 [IT] Italy ................................. MI94A1262

[51] Int. Cl.$^6$ ............................. A61K 9/20; A61K 9/28; A61K 9/48; A61K 9/56

[52] U.S. Cl. .................... 424/465; 424/451; 424/456; 424/463; 424/465; 424/494

[58] Field of Search ..................... 424/464, 465, 424/489, 474, 501, 466, 468, 451, 456, 463, 494; 514/568, 770, 781, 960, 576, 557, 570; 427/3

[56] References Cited

U.S. PATENT DOCUMENTS

| | | | |
|---|---|---|---|
| 4,681,897 | 7/1987 | Brand | 514/557 |
| 4,713,248 | 12/1987 | Kjorn et al. | 424/468 |
| 4,812,446 | 3/1989 | Brand | 514/165 |
| 4,831,058 | 5/1989 | Pankhania et al. | 514/570 |
| 4,839,176 | 6/1989 | Pankania | 424/465 |
| 5,164,398 | 11/1992 | Sims et al. | 514/282 |

*Primary Examiner*—Thurman K. Page
*Assistant Examiner*—Kathryn E. Shelborne
*Attorney, Agent, or Firm*—Nikaido, Marmelstein, Murray & Oram

[57] ABSTRACT

The present invention relates to a solid pharmaceutical composition containing (S)-2-(4-isobutylphenyl) propionic acid as active ingredient and it relates to a solid pharmaceutical composition suitable for the preparation of pharmaceutical forms in tablets, sachets and capsules containing (S)-2-(4-isobutylphenyl)-propionic acid as active ingredient. This formulation in tablets contains (S)-Ibupropen, colloidal silica as disintegrating agent, microcrystalline cellulose as diluent and magnesium stearate as lubricant. Tablets are prepared by direct compression of the pharmaceutical composition object of the present invention and may be coated or filmed according to conventional techniques.

21 Claims, No Drawings

SOLID PHARMACEUTICAL COMPOSITIONS CONTAINING (S)-2-(4-ISOBUTYLPHENYL) PROPIONIC ACID ACTIVE INGREDIENT AND MICROCRYSTALLINE CELLULOSE AND COLLOIDAL SILICA AS EXCIPIENTS

The present invention relates to a solid pharmaceutical composition containing (S)-2-(4-isobutylphenyl)propionic acid as active ingredient and, more particularly, it relates to a solid pharmaceutical composition suitable for the preparation of pharmaceutical forms in tablets, sachets and capsules, containing (S)-2-(4-isobutylphenyl)-propionic acid as active ingredient.

2-(4-Isobutylphenyl)propionic acid, which will be referred herein after to as the International Nonproprietary Name Ibuprofen, is a known non-steroidal anti-inflammatory drug (The Merck Index-XI Ed., No. 4812, page 476) used in therapy for its analgesic, antipyretic and anti-inflammatory activity.

Notwithstanding Ibuprofen is used in therapy from years in racemic form, it is known from some time that its active enantiomer is the one having (S) configuration, hereinafter referred to as (S)-Ibuprofen.

To the best of our knowledge, the first solid formulation of (S)-Ibuprofen described in literature is reported in example 1 of the European patent application No. 267321 (Medice Chem.-Pharm. Fabrik Puetter GmbH & Co.).

This formulation in tablets contains (S)-Ibuprofen (300 mg), insoluble polyvinylpyrrolidone (20 mg) as disintegrating agent, microcrystalline cellulose (150 mg) as diluent and magnesium stearate (10 mg) as lubricant.

In the same European patent application it is reported that the formulation of (S)-Ibuprofen in tablets or in other formulations suitable for the oral administration is carried out in a conventional way by using known diluents and carriers (page 3, lines 48–50).

Contrary to what stated in European patent application No. 267321, the formulation of (S)-Ibuprofen in tablets, or in solid pharmaceutical forms in general, is a problem anything but conventional and difficult to solve by using common excipients and carriers.

In fact, as widely reported in literature, the formulation of (S)-Ibuprofen in solid pharmaceutical forms such as tablets, sachets and capsules shows considerable drawbacks mainly due to the low melting point of (S)-Ibuprofen (51°–55° C.) and to the formation of eutectic mixtures with usual excipients (see for example Romero A. J. et al., Drug Development and Industry Pharmacy, 17(5), 777–792 (1991) e Romero A. J. et al., J. Pharm. Belg., 1993, 48, 1, 27–32). In fact, these physical features of the active ingredient make difficult the mixture and the compression of the powders.

Some solid formulation containing (S)-Ibuprofen have been described in literature.

European patent No. 478838 and International patent application No. WO 93/23026, both in the name of Pharmatrans Sanaq AG, disclose (S)-Ibuprofen compositions with improved properties of compression due to the use of the active ingredient in the form of its calcium salt.

Analogously, International patent applications WO 92/20334 and WO 94/10994 (The Boots Company PLC) disclose pharmaceutical compositions containing (S)-Ibuprofen as salt, in particular as sodium salt.

Obviously the use of (S)-Ibuprofen in the form of a salt allows to increase the melting point and to avoid the formulation problems specifically bound to the low melting temperature of the active ingredient.

International patent application WO 93/04676 (The Boots Company PLC) discloses (S)-Ibuprofen formulations prepared by using agglomerates containing (S)-Ibuprofen (70–97% by weight) and starch (3–30% by weight).

European patent application No. 398287 (Medice Chem.-Pharm. Fabrik Puetter GmbH & Co.) discloses solid solutions of (S)-Ibuprofen in low melting polyethyleneglycols or polyethyleneoxides useful for filling hard gelatine capsules.

The use of low melting excipients allows the preparation of a melted mixture which is directly poured into the capsules where at room temperature it solidifies.

This kind of formulation cannot be used for the preparation of tablets or sachets.

International patent application WO 94/10993 (Nycomed Dak A/S) discloses pharmaceutical formulations containing (S)-Ibuprofen (40–70% by weight), a hydrosoluble ligand different from polyvinylpyrrolidone and optionally silica in amounts not higher than 2%.

To the best of our knowledge, only one formulation of (S)-Ibuprofen as filmed tablets is on the market (Seractil®— commercialized in Austria by Gebro Broschek GmbH).

We have now found a pharmaceutical composition containing (S)-Ibuprofen as free acid which has good flowability, good compactability and compressibility and which is particularly suitable for the preparation of tablets, sachets and hard gelatine capsules.

It is therefore the object of the present invention a solid pharmaceutical composition containing 50–70% by weight of (S)-Ibuprofen, 30–50% by weight of microcrystalline cellulose, colloidal silica in an amount lower than 0.3% by weight, a lubricant in an amount lower than 0.3 by weight and optionally a wetting agent or a surfactant, the total being 100%.

The composition object of the present invention can be prepared by direct mixing and is characterized by a good flowability, compactability and compressibility which make it particularly suitable for the preparation of tablets and for the filling of sachets and hard gelatine capsules.

(S)-Ibuprofen is present as free acid.

The amount of (S)-Ibuprofen in the pharmaceutical compositions object of the invention is preferably between 55% and 65% by weight. Still more preferably, the amount of (S)-Ibuprofen is between 58% and 62% by weight.

The amount of microcrystalline cellulose in the pharmaceutical composition object of the invention is preferably between 35% and 45% by weight.

Still more preferably, the amount of microcrystalline cellulose is between 38% and 42% by weight.

A specific example of microcrystalline cellulose is Avicel® (registered trade mark of FMC Corporation).

The amount of colloidal silica in the composition object of the invention is preferably between 0.01% and 0.3% by weight.

Still more preferably, the amount of colloidal silica is between 0.1% and 0.3%.

Specific examples of colloidal silica are Aerosil® 200 and Aerosil® 380 (registered trade marks of Degussa A. G.).

The lubricant present in the compositions object of the invention is preferably magnesium stearate.

The lubricant is preferably present in an amount between 0.01% and 0.3%, still more preferably between 0.05% and 0.3%.

When present, the wetting agent is in an amount between 3% and 6% by weight.

Examples of wetting agents suitable in the pharmaceutical compositions object of the present invention are solid polyethylene glycols (The Merck Index—XI Ed., No. 7545, page 1204) and poloxamers (The Merck Index—XI Ed., No. 7537, page 1203).

When present, the surfactant is in an amount between 0.01% and 2% by weight.

Examples of surfactants suitable in the pharmaceutical compositions of the present invention are sodium lauryl sulfate, octoxynol (The Merck Index—XI Ed., No. 6681, pages 1070–1), Span® and Tween® (The Merck Index—XI Ed., No. 8689, page 1377). Span® and Tween® are trade marks of ICI Americas Inc.

Specific examples of solid pharmaceutical compositions object of the present invention are the following.

A) A pharmaceutical composition formed by (percentages by weight):

| | |
|---|---|
| (S)-Ibuprofen | 62.1% |
| Microcrystalline cellulose | 37.5% |
| Colloidal silica | 0.2% |
| Magnesium stearate | 0.2% |

B) A pharmaceutical composition formed by (percentages by weight):

| | |
|---|---|
| (S)-Ibuprofen | 66.4% |
| Microcrystalline cellulose | 33.2% |
| Colloidal silica | 0.3% |
| Magnesium stearate | 0.2% |

C) A pharmaceutical composition formed by (percentages by weight):

| | |
|---|---|
| (S)-Ibuprofen | 58.8% |
| Microcrystalline cellulose | 40.9% |
| Colloidal silica | 0.2% |
| Magnesium stearate | 0.1% |

D) A pharmaceutical composition formed by (percentages by weight):

| | |
|---|---|
| (S)-Ibuprofen | 66.5% |
| Microcrystalline cellulose | 33.2% |
| Colloidal silica | 0.1% |
| Magnesium stearate | 0.2% |

E) A pharmaceutical composition formed by (percentages by weight):

| | |
|---|---|
| (S)-Ibuprofen | 58.8% |
| Microcrystalline cellulose | 40.7% |
| Colloidal silica | 0.3% |
| Magnesium stearate | 0.2% |

The pharmaceutical compositions object of the present invention are prepared by direct mixing of the powders.

The resultant mixture can be used for filling sachets or hard gelatine capsules or, more preferably, it can be used for the preparation of tablets.

In particular, from a practical point of view, the solid pharmaceutical composition object of the present invention is used as such for the filling of hard gelatine capsules while it is preferably added to further excipients like sweeteners, sweetening agents and flavoring agents before being used for the filling of the sachets. The addition of further excipients is carried out by direct mixing. The suitability of the pharmaceutical compositions object of the present invention for the filling of capsules and sachets has been verified by evaluating their physical characteristics too.

In particular, the angle of repose of the pharmaceutical compositions of the present invention, a significative index of the flowability of the powder mixtures and therefore their suitability to the productive work-up was evaluated (example 9).

Tablets are prepared by direct compression of the pharmaceutical composition object of the present invention and may be optionally coated or filmed according to conventional techniques.

It is worth noting that during the compression of the compositions object of the present invention phenomenons of adhesiveness to tablet-press punches are not observed.

Furthermore, the obtained tablets are endowed with good hardness and with a very good friability value (example 10).

It is evident to the man skilled in the art the importance of these technological parameters for the industrial preparation of finished dosage forms.

In fact, in the specific case of the use of (S)-Ibuprofen as free acid for the preparation of solid pharmaceutical forms, these parameters are particularly unexpected because the literature teaches that tablets of (S)-Ibuprofen are difficult to prepare and, according to our knowledge, the unique known examples of formulation of (S)-Ibuprofen in tablets necessarily provide for the use of a ligand, in particular of a water-soluble ligand such as polyvinylpyrrolidone, as described in the above cited paper published on J. Pharm. Belg., or such as starch, gelatine and the like, as disclosed in the above cited international patent applications No. WO 94/10993 and WO 93/04676.

It is worth noting in this respect that the solid pharmaceutical compositions object of the present invention not only do not need the use of any kind of ligand, but they are essentially formed by the active ingredient, as main component, and by a diluent (microcrystalline cellulose).

In addition to good physical characteristics, the tablets object of the present invention show very good biopharmaceutical characteristics.

In fact, the tablets object of the invention disintegrate quickly (within 3–5 minutes) and the dissolution of the active ingredient is extremely fast, also in comparison with the only formulation on the market (example 11).

In this case too it is evident to the man skilled in the art the importance of these biopharmaceutical parameters which allow to the active ingredient to be bioavailable, and therefore therapeutically effective, in the shortest time possible.

The pharmaceutical forms in tablets, sachets and capsules prepared with the solid pharmaceutical compositions object of the invention represent a further object of the present invention.

The pharmaceutical forms in tablets, sachets or capsules prepared with the compositions object of the present invention contain an amount of active ingredient equal to 50 mg, 100 mg, 150 mg, 200 mg, 300 mg or 400 mg by tablet, by sachet or by capsule.

Preferably, the amount of active ingredient is equal to 200 mg or 300 mg.

With the aim to illustrate the present invention the following examples are now given.

EXAMPLE 1

A pharmaceutical composition having the following composition

| | |
|---|---|
| (S)-Ibuprofen | 20 kg |
| Avicel ® | 13.85 kg |
| Aerosil ® 200 | 0.1 kg |
| Magnesium stearate | 0.5 kg | was prepared according the following procedure.

(S)-Ibuprofen was sieved together with Avicel® through a 1 mm sieve. Then the powders were mixed in a cubic mixer for 10 minutes. Magnesium stearate and Aerosil® were sieved and added to the preceding mixture. Then the whole was mixed for 5 minutes.

EXAMPLE 2

A pharmaceutical composition having the following composition:

| | |
|---|---|
| (S)-Ibuprofen | 30 kg |
| Avicel ® | 20.85 kg |
| Aerosil ® 200 | 0.1 kg |
| Magnesium stearate | 0.05 kg | was prepared according the procedure described in the example 1.

EXAMPLE 3

A pharmaceutical composition, prepared as described in example 1, was used for the preparation of tablets of 340 mg of weight, containing 200 mg of active ingredient, according to the following procedure.

The mixture was set on a rotary tablet-press fed by gravity, equipped by 18 biconcave punches having 10 mm diameter. Compression speed: 50,000 tablets/hour.

EXAMPLE 4

A pharmaceutical composition, prepared as described in example 2, was used for the preparation of tablets of 510 mg of weight, containing 300 mg of active ingredient, according to the following procedure.

The mixture was set on a rotary tablet-press provided with forced loading, equipped by 18 biconcave punches having 13 mm diameter. Compression speed: 60,000 tablets/hour.

EXAMPLE 5

A pharmaceutical composition, prepared as described in example 2, was used for the preparation of tablets of 680 mg of weight, containing 400 mg of active ingredient, according to the following procedure.

The mixture was set on a rotary tablet-press provided with forced loading, equipped by 18 biconcave capsule-shaped punches (16×8 mm).

Compression speed: 60,000 tablets/hour.

EXAMPLE 6

Tablets, prepared as described in example 3, were set into a coating pan and covered with a filming solution having the following composition (percentage by weight):

| | |
|---|---|
| Hydroxypropyl cellulose | 3% |
| Polyethyleneglycol 6000 | 0.9% |
| Sodium saccharine | 0.03% |
| Distilled water | q.s. to 100% |

The increasing in weight of the coated tablets was about 1% (w/w).

EXAMPLE 7

A pharmaceutical composition, prepared as described in example 1, was used for the preparation of hard gelatine capsules, containing 340 mg of mixture equivalent to 200 mg of (S)-Ibuprofen, according to the following procedure.

The powders were set on a rotative capsulating machine equipped with "0" size molds.

Production speed: 30,000 capsules/hour.

EXAMPLE 8

A pharmaceutical composition, prepared as described in example 2, was used for the preparation of sachets.

Saccharose (103.5 kg), saccharine (2 kg) and orange flavor (10 kg) were added to the mixture (51 kg).

The resultant mixture was packed by an automatic packaging machine into sachets each containing 1.5 g of mixture, equivalent to 200 mg of (S)-Ibuprofen.

EXAMPLE 9

Mixtures prepared as described in examples 1, 2 and 8 were characterized from a physical point of view with the aim to verify their suitability to the productive work-up, by flowability test.

For the determination the method reported in "Pharmaceutical Dosage Forms-Tablets", vol. 1, page 45, edited by Herbert A. Liberman and Leon Lochman—Marcel Dekker, Inc.-New York-1980 was used.

The flowability index, expressed as angle of repose, for each powder mixtures is reported in the following table 1.

TABLE 1

Flowability index, expressed as angle of repose, of the mixtures prepared as described in examples 1, 2 and 8

| Example | Angle of repose |
|---|---|
| 1 | 36°15' |
| 2 | 39°50' |
| 8 | 35°10' |

The above mentioned angles of repose were lower than 45°, the limit value over which the flowability index of powder mixtures was not considered acceptable for the productive work-up.

EXAMPLE 10

Tablets and coated tablets, prepared as described in examples 3, 4, 5 and 6, were characterized from a physical point of view to verify their suitability to the productive work-up, by hardness test and by friability test.

The hardness was determined by using the proper equipment made by Dr. K. Schleuniger & Co.

The friability was determined by using the Roche friability (Remington's—Pharmaceutical Sciences, Ed. 1980, page 1558—Mack Publishing Company).

The hardness and friability values of the tablets prepared as described in examples 3, 4, 5 and 6 are reported in the following table 2.

TABLE 2

Hardness values, expressed as kilopond (kp), and friability values, expressed in percentage (w/w) of tablets prepared as described in examples 3, 4, 5 and 6.

| Example | Hardness (kp) | Friability (%) |
|---|---|---|
| 3 | 4–6 | 0.3 |
| 4 | 5–7 | 0.2 |
| 5 | 8–9 | 0.3 |
| 6 | 6–8 | 0 |

The obtained hardness values were higher than the minimum values considered acceptable for tablets of analogous weight and diameter. The friability values were strongly lower than 2%, the maximum limit over which tablets are not considered acceptable.

EXAMPLE 11

Tablets, coated tablets, capsules, sachets, prepared as described in examples 3, 4, 5, 6, 7 and 8 and the tablets commercialized as Seractil®, containing 200 mg of (S)-Ibuprofen, were evaluated from a bioavailability point of view.

Dissolution

Dissolution time of the active ingredient was determined for all the different pharmaceutical forms by the method described in the USP XXII, page 683 and by using the equipment described in the USP XXII, pages 1578–9, Apparatus 1.

The obtained dissolution time values of 90% active ingredient are reported in the following table 3.

TABLE 3

Dissolution time of 90% of (S)-Ibuprofen (T90), expressed in minutes, obtained for tablets, coated tablets, capsules and sachets, prepared as described in examples 3, 4, 5, 6, 7 and 8 in comparison with Seractil ® (200 mg).

| Example | Dissolution time (T90) (minutes) |
| --- | --- |
| 3 | 3'30" |
| 4 | 4'20" |
| 5 | 5'10" |
| 6 | 6'00" |
| 7 | 5'10" |
| 8 | 3'00" |
| Seractil ® | 19' |

The dissolution times of the pharmaceutical forms object of the present invention allow a quick bioavailability of the active ingredient and they are remarkably lower than (S)-Ibuprofen tablets on the market.

Disintegration

Disintegration time for the pharmaceutical forms in tablets, coated tablets and capsules object of the present invention was evaluated according to the method described in the USP XXII, pages 1577–1578. The obtained disintegration times are reported in the following table 4.

TABLE 4

Disintegration times, expressed in seconds, obtained for the tablets, coated tablets and capsules, prepared as described in examples 3, 4, 5, 6 and 7.

| Example | Disintegration time (seconds) |
| --- | --- |
| 3 | 45 |
| 4 | 80 |
| 5 | 105 |
| 6 | 180 |
| 7 | 180 |

The above mentioned disintegration times were very rapid and lower than three minutes for the coated tablets too.

It is claimed:

1. A solid pharmaceutical composition consisting of 50–70% by weight of (S)-Ibuprofen, 30–50% by weight of microcrystalline cellulose, colloidal silica in an amount lower than 0.3% by weight, a lubricant in an amount lower than 0.3% by weight and optionally a wetting agent or a surfactant, the total being 100% with the proviso that the composition does not contain polyethylene glycol as a water-soluble binder.

2. A solid pharmaceutical composition according to claim 1 wherein the amount of (S)-Ibuprofen is between 55% and 65% by weight.

3. A solid pharmaceutical composition according to claim 1 wherein the amount of (S)-Ibuprofen is between 58% and 62% by weight.

4. A solid pharmaceutical composition according to claim 1 wherein the amount of microcrystalline cellulose is between 35% and 45% by weight.

5. A solid pharmaceutical composition according to claim 1 wherein the amount of microcrystalline cellulose is between 38% and 42% by weight.

6. A solid pharmaceutical composition according to claim 1 wherein the amount of colloidal silica is between 0.01% and 0.3% by weight.

7. A solid pharmaceutical composition according to claim 1 wherein the amount of colloidal silica is between 0.1% and 0.3% by weight.

8. A solid pharmaceutical composition according to claim 1 wherein the lubricant is magnesium stearate.

9. A solid pharmaceutical composition according to claim 1 wherein the amount of lubricant is between 0.01% and 0.3%.

10. A solid pharmaceutical composition according to claim 1 wherein the amount of lubricant is between 0.05 and 0.3%.

11. A solid pharmaceutical composition according to claim 1 wherein the wetting agent when present is in an amount between 3% and 6% by weight.

12. A solid pharmaceutical composition according to claim 1 wherein the surfactant when present is in an amount between 0.01% and 2%.

13. A solid pharmaceutical composition having the following composition (percentage by weight)

| | |
| --- | --- |
| (S)-Ibuprofen | 62.1% |
| Microcrystalline cellulose | 37.5% |
| Colloidal silica | 0.2% |
| Magnesium stearate | 0.2% |

14. A solid pharmaceutical composition having the following composition (percentage by weight)

| | |
| --- | --- |
| (S)-Ibuprofen | 66.4% |
| Microcrystalline cellulose | 33.2% |
| Colloidal silica | 0.3% |
| Magnesium stearate | 0.2% |

15. A solid pharmaceutical composition having the following composition (percentage by weight)

| | |
| --- | --- |
| (S)-Ibuprofen | 58.8% |
| Microcrystalline cellulose | 40.9% |
| Colloidal silica | 0.2% |
| Magnesium stearate | 0.1% |

16. A solid pharmaceutical composition having the following composition (percentage by weight)

| | |
| --- | --- |
| (S)-Ibuprofen | 66.5% |
| Microcrystalline cellulose | 33.2% |
| Colloidal silica | 0.1% |
| Magnesium stearate | 0.2% |

17. A solid pharmaceutical composition having the following composition (percentage by weight)

| | |
|---|---|
| (S)-Ibuprofen | 58.8% |
| Microcrystalline cellulose | 40.7% |
| Colloidal silica | 0.3% |
| Magnesium stearate | 0.2% |

18. A pharmaceutical form in tablet, sachet or capsule prepared by using a pharmaceutical composition according to claim 1.

19. A pharmaceutical form according to claim 18 in tablet coated or filmed.

20. A pharmaceutical form according to claim 18 consisting of an amount of (S)-Ibuprofen of 50 mg, 100 mg, 150 mg, 200 mg, 300 mg or 400 mg.

21. A pharmaceutical form according to claim 18 consisting of an amount of (S)-Ibuprofen of 200 mg or 300 mg.

* * * * *